United States Patent [19]

VanDerBel

[11] Patent Number: 4,597,383

[45] Date of Patent: Jul. 1, 1986

[54] FIBER-OPTIC ILLUMINATED VAGINAL SPECULUM

[75] Inventor: Frans G. VanDerBel, Southbridge, Mass.

[73] Assignee: Luxtec Corporation, Sturbridge, Mass.

[21] Appl. No.: 727,400

[22] Filed: Apr. 25, 1985

[51] Int. Cl.⁴ .............................................. A61B 1/30
[52] U.S. Cl. ....................................................... 128/18
[58] Field of Search ....................................... 28/18, 17

[56] References Cited

U.S. PATENT DOCUMENTS

| 3,716,047 | 2/1973 | Moore et al. | 128/18 |
| 3,789,835 | 2/1974 | Whitman | 128/18 |
| 4,562,832 | 1/1986 | Wilder et al. | 128/18 X |

*Primary Examiner*—William H. Grieb
*Attorney, Agent, or Firm*—Blodgett & Blodgett

[57] ABSTRACT

Vaginal speculum comprising a supporting base and a pair of parallel elongated separable jaws operatively connected to the base and fiber-optic illumination means operatively connected to the speculum for projecting a light beam within a viewing channel which is defined between the separated jaws of the speculum.

11 Claims, 9 Drawing Figures

FIBER-OPTIC ILLUMINATED VAGINAL SPECULUM

BACKGROUND OF THE INVENTION

This invention relates to a vaginal speculum which is provided with illumination means and to an illumination attachment for a vaginal speculum.

Vaginal speculums are commonly used by gynecologists for internal examinations of female genitalia. The speculum consists of a supporting base element, a fixed jaw element which is adjustably slidably mounted on the base element and an elongated movable jaw. The fixed jaw element includes an elongated fixed jaw which extends at a right angle to the base. The movable jaw extends substantially parallel to the fixed jaw and is pivotally mounted on the base for pivoting movement toward and away from the fixed jaw. The jaws define, therebetween, an elongated viewing channel when the jaws are separated.

During vaginal examination, the jaws are inserted within the vagina in the closed position. The movable jaw is provided with a lever which enables the physician to move the movable jaw away from the fixed jaw to force the walls of the vagina apart and to form a viewing channel between the jaws. The speculum is generally provided with an adjustable stop which maintains the movable jaw in the open position so that the speculum can be released by the physician and will remain in place in the open viewing position. In order to make a proper examination, lighting must be provided. Since the physician's hands must be free for the examination for other tasks such as applying pressure on the abdomen, the assisting nurse must hold and focus the light. However, the nurse has other duties to perform, such as helping to support the patient and providing the physician with various materials which are normally associated with a vaginal examination. The holding of a light seriously interfers with the nurse's ability to efficiently assist the physician. In addition, conventional sources of light are unsatisfactory in terms of providing sufficient illumination within the viewing channel. For example, the light provided by an ordinary flashlight is generally not intense enough and the flashlight must be positioned precisely in order to focus into the viewing channel which means that the flashlight represents a viewing obstacle to the physician. The use of more intense lighting is counter-productive since the glare which is created around the speculum tends to cancel out whatever extra illumination which is provided within the viewing channel. Also, the existence of bright lights is disturbing to the patient who is likely to be nervous and self-conscious by the examination itself. These and other difficulties experienced with the prior art speculums have been obviated by the present invention.

It is, therefore, a principle object of the invention to provide a vaginal speculum which is provided with fiber-optic illumination means which provides sufficient viewing light for examination and which does not interfere with the physician's ability to view the area which is being examined.

Another object of this invention is the provision of a fiber-optics illumination attachment for a vaginal speculum which provides sufficient viewing light for examination and which does not interfere with the physician's ability to view the area which is being examined.

A further object of the present invention is the provision of a fiber-optic illumination means for a vaginal speculum which concentrates a light beam in the center of the viewing channel which is formed by the speculum without obstructing the viewing channel.

It is another object of the present invention to provide a fiber-optic illumination attachment for a vaginal speculum which includes means for mounting the attachment to the speculum so that the attachment is accurately positioned on the speculum for directing a light beam along the center of the viewing channel which is formed by the speculum.

A still further object of the invention is the provision of a vaginal speculum which includes a fiber-optic illumination means which is simple in construction, and which is capable of a long life of useful service with a minimum of maintenance.

It is a further object of the invention to provide a vaginal speculum which includes a fiber-optic illumination device which provides a maximum concentrated illumination which does not interfere with the physician's ability to view the area of examination or to create excessive brightness outside of the viewing area which might tend to be distracting to a physician and disturbing to the patient.

With these and other objects in view, as will be apparent to those skilled in the art, the invention resides in the combination of parts set forth in the specification and covered by the claims appended hereto.

SUMMARY OF THE INVENTION

In general, the invention consists of a vaginal speculum comprising a supporting base, an elongated fixed jaw which is mounted on the supporting base and extends at a right angle from the supporting base, an elongated movable jaw which is pivotedly mounted on the supporting base and extends generally parallel with the fixed jaw to form, therebetween, a viewing channel, an elongated fiber-optic guide tube which is mounted on the supporting base and which is adapted for projecting a beam of light along said viewing channel. The invention also comprises a fiber-optic light attachment for a vaginal speculum which is adapted to be mounted on the base portion of a conventional speculum and which is adapted for projecting a beam of light within the viewing channel which is formed between the jaws of the speculum.

BRIEF DESCRIPTION OF THE DRAWINGS

The character of the invention, however, may be best understood by the reference to one of its structural forms, as illustrated by the accompanying drawings, in which.

DETAILED DESCRIPTION OF THE INVENTION

Figure 1:
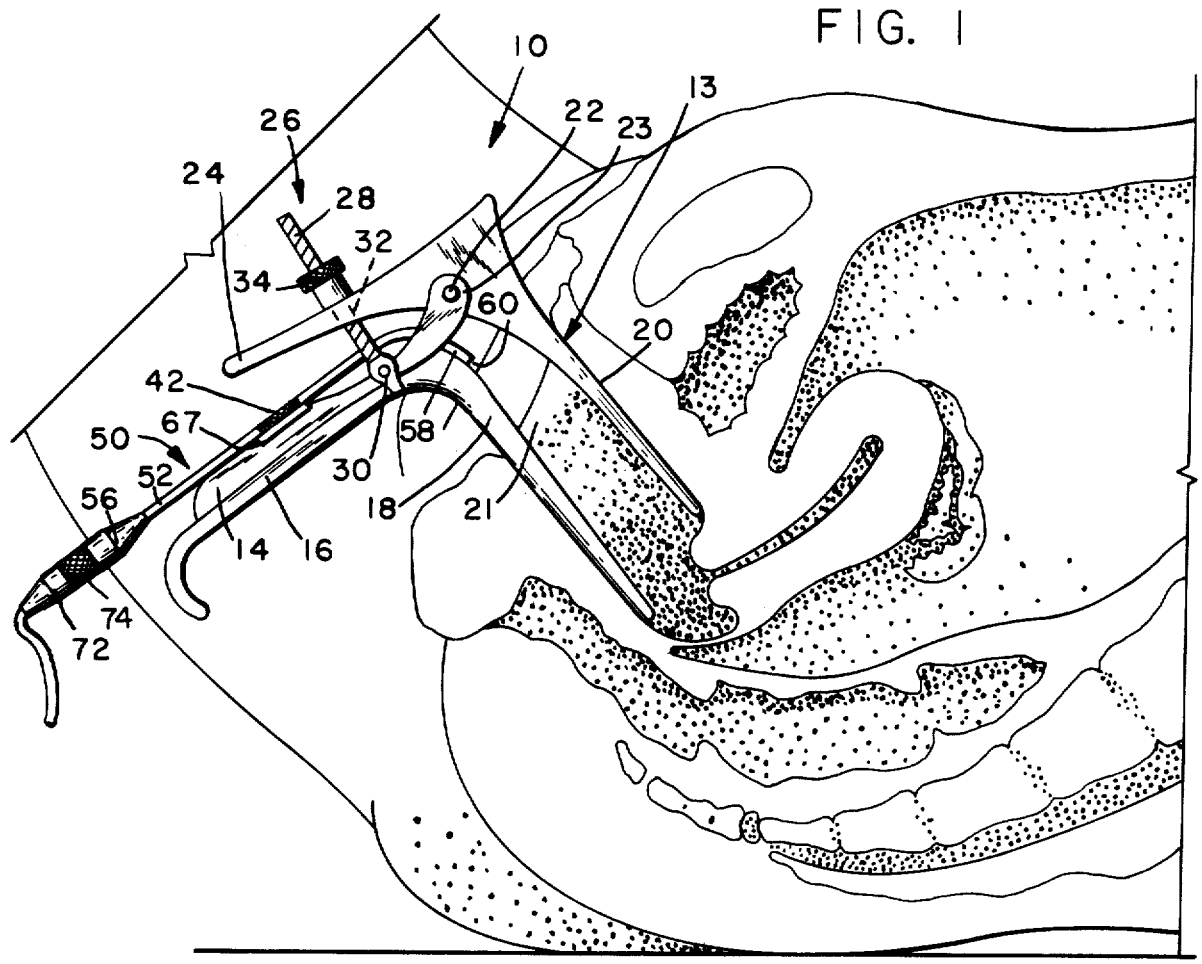
FIG. 1 is a side elevational view of a vaginal speculum embodying the principles of the present invention and shown in use within a vaginal opening.
Figure 2:
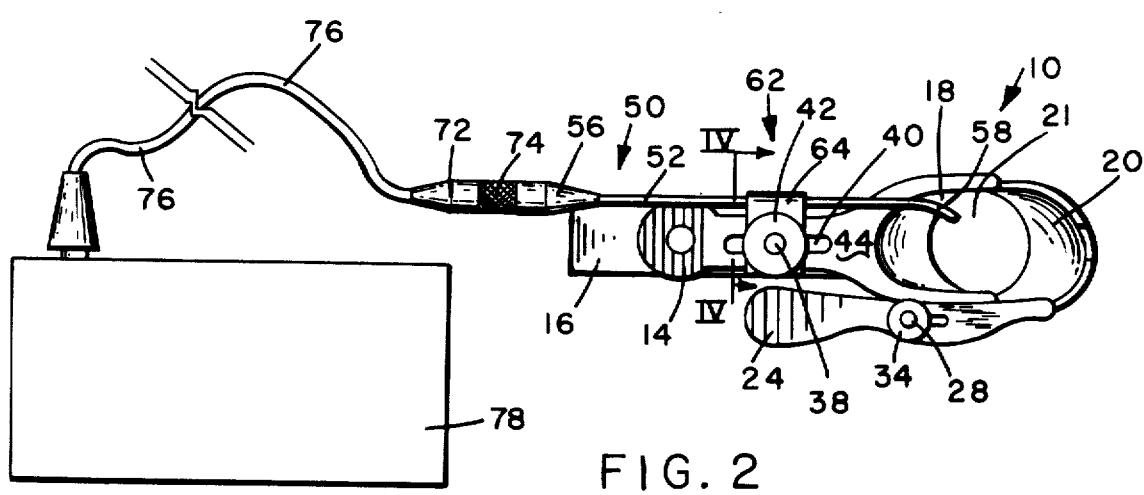
FIG. 2 is a plan view of the speculum.
Figures 3, 4, 5, 6, 7:
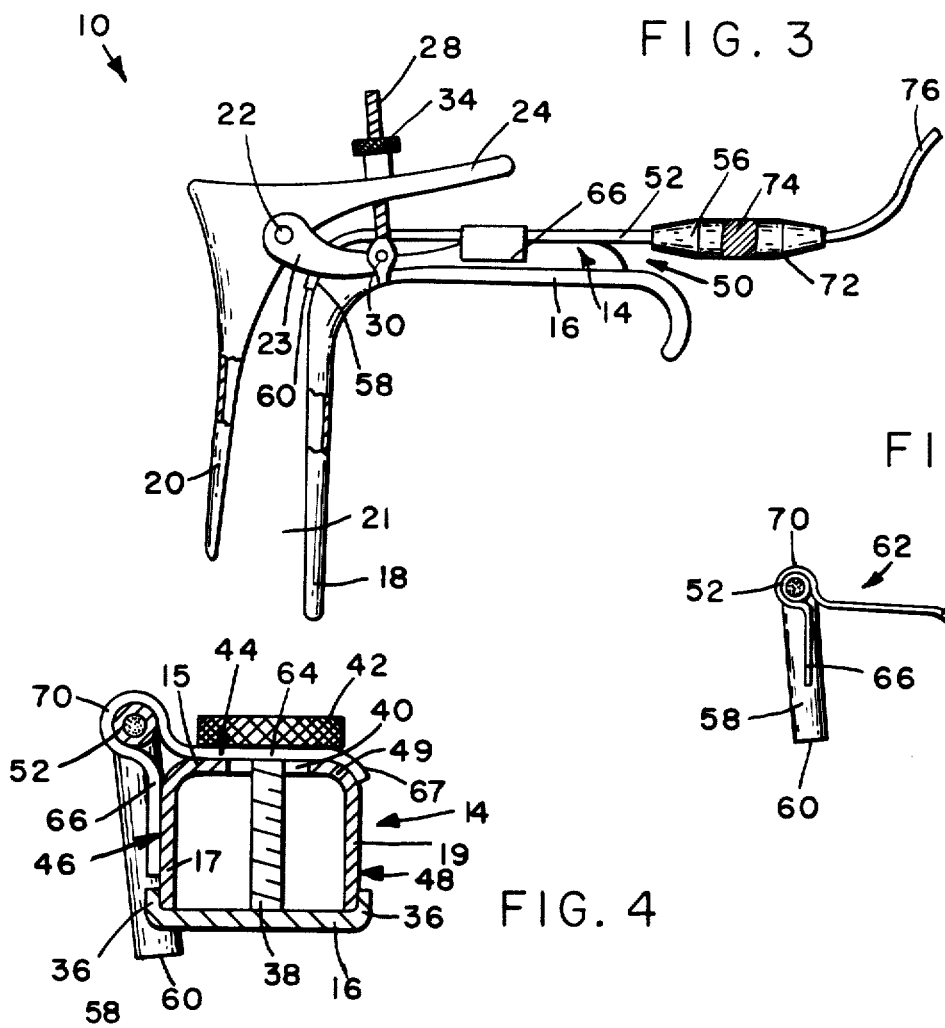
FIG. 3 is a side elevational view of the opposite side of the speculum from that which is shown in FIG. 1.
FIG. 4 is a vertical cross-sectional view of the speculum taken on the line IV—IV of FIG. 2, on an enlarged scale.
FIG. 5 is a side elevational view of a fiber-optic illumination portion of the speculum.
FIG. 6 is a plan view of the fiber-optic illumination portion of the speculum.
FIG. 7 is an end elevational view of the illumination portion of the speculum.

Referring first to FIGS. 1-4, the speculum of the present invention is generally indicated by the reference numeral 10 and is shown in FIG. 1 in operational condition within a vaginal opening. The speculum 10 comprises a supporting base 14, a fixed jaw element 16 and a movable jaw element 13. The supporting base 14 is U-shaped in cross-section as shown in FIG. 4 and comprises an upper wall 15 and two side walls 17 and 19. The fixed jaw element 16 includes an elongated fixed jaw 18 which extends at a right angle to the main portion of the fixed jaw element and to the supporting base 14. The movable jaw element 13 is pivotally mounted between a pair of forwardly extending arms 23 of the base 14 by means of pivot pins 22. The movable jaw element 13 includes an elongated movable jaw 20 which extends at a right angle to the supporting base and extends generally parallel with the fixed jaw 18 to define, therebetween, an elongated viewing channel 21. The movable jaw element 13 also includes a lever 24. The lever 24 and the movable jaw 20 constitutes a bell crank lever, whereby the movable jaw 20 may be moved toward and away from the fixed jaw 18 by actuating the lever 24. The jaws 18 and 20 are inserted within the vaginal opening in the closed position and the opening is distended by applying downward pressure on the lever 24 to pivot the movable jaw 20 away from the fixed jaw 18 as shown in FIG. 1. The jaw 20 is maintained in the open position by adjustable stop means, generally indicated by the reference numeral 26. The stop means 26 includes a threaded rod 28 which is pivotally attached to the supporting base 14 by a pin 30. The rod 28 extends freely through an aperture 32 in the lever 24. A nut 34 is threaded onto the screw 28 so that when the movable jaw 20 is in the desired open position, the nut 34 is advanced downwardly along the screw 28 until it engages the upper surface of the lever 24. This prevents the movable jaw 20 from moving toward the fixed jaw 18.

Referring particularly to FIG. 4, the fixed jaw element 16 is mounted on the supporting base 14 for sliding axial adjustment. The fixed jaw element 16 includes a pair of upperwardly extending guide rails 36 which stradle the side walls 17 and 19 of the supporting base. A screw 38 extends upwardly from a fixed position on the fixed jaw element 16 through an elongated slot 40 in the upper wall 15 of the supporting base 14 and extends above the wall 15. A nut 42 is threaded onto the upper end of the screw 38 and functions to clamp firmly the fixture element 16 to the supporting base 14. The fixture element 16 can be adjusted axially relative to the supporting base 14 by loosening the screw 42 and axially sliding the guide rails 36 along the bottom edges of the side walls 17 and 19. Since the movable jaw element is pivotally attached to the supporting base, adjustment of the fixed jaw element 16 relative to the supporting base also changes the spatial relationship between the fixed jaw element 16 and the movable jaw element 13. The top wall 15 has a first outer surface 44. The side wall 17 has a second outer surface 46 and a third side wall 19 has a third outer surface 14. The outer surfaces 44, 46, and 48 are all generally flat and the surfaces 14 and 46 extend at a right angle to the surface 44. The junctures between each of the side walls 17 and 19 and the upper wall 15 are rounded so that a curved outer surface 49 connects the first surface 44 to the third surface 48.

All of the elements which have been described so far represent a conventional state of the art vaginal speculum. The fiber-optic illumination means which is to be described represents the improved aspects of the speculum of the present invention. The fiber-optic illumination means to be described is depicted as an attachment to an existing speculum which requires no modification of the speculum. The fiber-optic illumination system is generally indicated by the reference numeral 50 and comprises an elongated fiber-optic guide tube, generally indicated by the reference numeral 52. The tube 52 includes an elongated straight portion which terminates at an open end 54. The opposite end of the tube 52 has a curved portion 58 which terminates at an open end 60. The tube 52 contains a bundle of light transmitting or optical fibers which extend from the end 54 to the end 60. The end 54 is adapted to be attached to an industry standard male coupling element 56 which, in turn, is adapted to be operatively connected to a male coupling element 72 by means of a coupling nut 74. The coupling nut 72 is attached to a fiber-optic cable 76 which is, in turn, connected to a standard fiber-optic light source 78. For example, good results have been obtained with a Model Lux 1150 of Luxtec Corporation. When the tube 52 is connected to the light source 78, light is transmitted through the fiber bundles in the cable 76 and the tube 52 and projects as a light beam from the open end 60 of the tube 52. An L-shaped mounting bracket, generally indicated by the reference numeral 62, is mounted on the tube 52 and includes a first horizontal leg 64 and a second vertical leg 66. The legs 64 and 66 are formed from a single length of sheet metal which is bent into a loop 70 between the legs. The loop 70 is crimped tightly about the tube 52 as shown in FIG. 7 so that the legs 64 and 66 maintain a specific orientation relative to the bent portion 58 of the tube.

The first horizontal flat leg 64 includes a slot 68 and is adapted to rest on top of the first upper surface 44 of the supporting base 14, as shown in FIG. 4, so that the screw 38 extends through the slot 68. The second vertical leg 66 is adapted to abut the second surface 46 of the supporting base. The leg 64 of the mounting bracket 62 is clamped firmly between the nut 42 and the upper wall 15 of the supporting base. The surfaces 44 and 46 function as locating surfaces for the legs 64 and 66, respectively, which enable the tube 52 to assume a predetermined specific orientation relative to the fixed jaw 18 as shown in FIGS. 1 and 2. As shown in FIG. 1, the bent portion 58 of the tube extends downwardly into the upper part of the viewing channel 21 so that the open end 60 faces downwardly toward the center of the channel. As shown in FIG. 2, the tube 58 is further orientated so that the bent portion 58 is located at the rearward end of the viewing channel and to one lateral side of the viewing channel. The orientation of the bent portion 58 is such that the opening 60 faces forwardly and laterally toward the center of the viewing channel as well as downwardly. This enables a light beam from the open end 60 to project into the center of the viewing channel without obstructing the viewing channel to observation by the physician. The orientation of the open end 60 of the guide tube 52 relative to the viewing channel 21 is shown more graphically in FIGS. 8 and 9.

Figure 8:
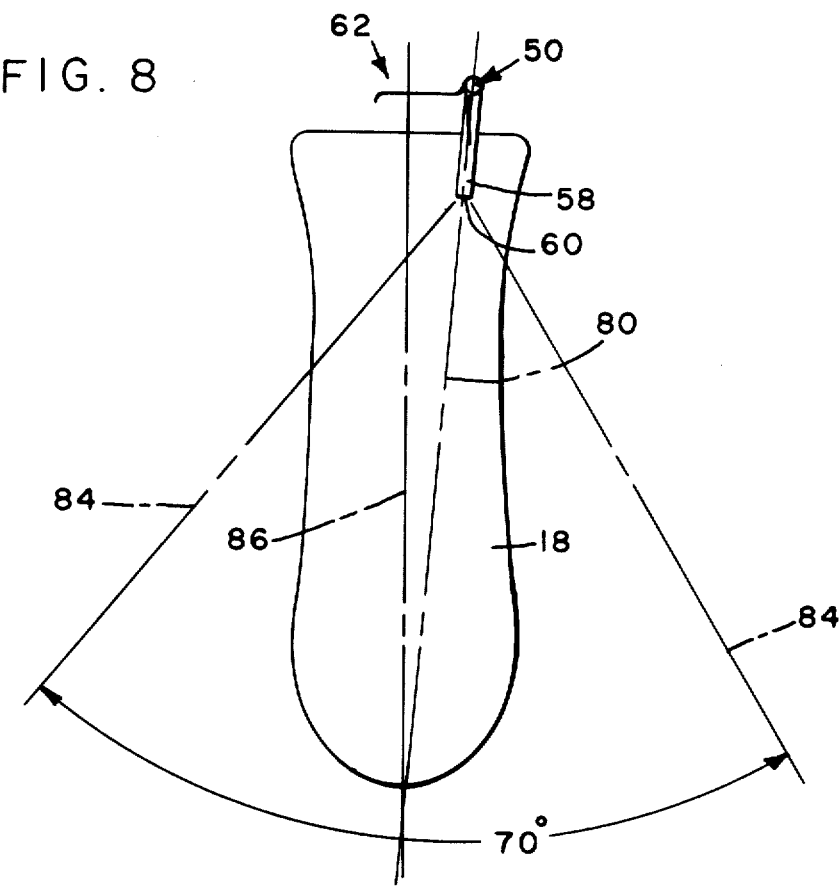
FIG. 8 is a diagramatic view showing the focusing relationship of the fiber-optic light beam relative to one jaw of the speculum.

Referring particularly to FIG. 8, the end 60 of the tube 52 is positioned relative to the fixture 18 so that it is located near one side of the jaw and faces downwardly toward a point which is at the center and bottom of the viewing channel. The central axis of the light beam which emanates from the open end 60 is indicated by the dot-and-dash line 80. The axis 80 is at an angle to the central vertical axis 86 of the viewing channel 21 and intersects the viewing channel at the bottom of the channel. Although light is concentrated along the center of the jaw, the light beam spreads at an angle of approximately 70°, the beam being indicated by the dot-and-dash lines 84.

Figure 9:
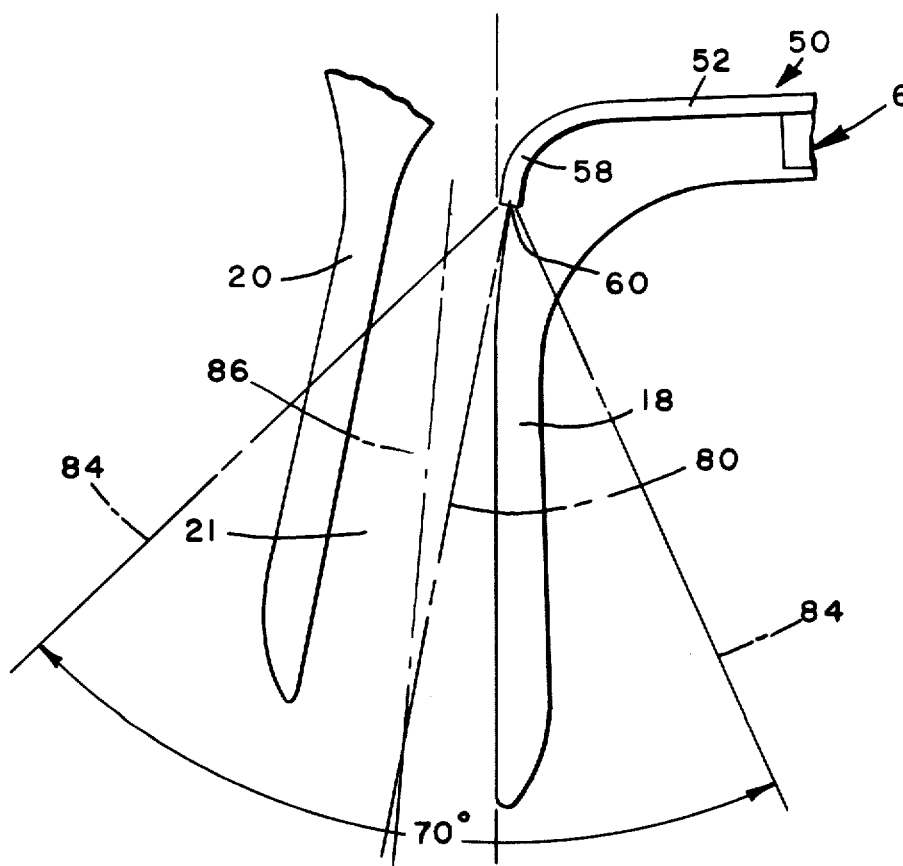
FIG. 9 is a diagramatic view showing the relationship between the fiber-optic light beam and the viewing channel which is formed by the jaws of the speculum.

Referring to FIG. 9, which is a view looking in from the side of the viewing channel 21, the open end 60 of the guide tube 52 is orientated so that the central axis 80 of the light beam projects downwardly and forwardly within the channel 21. As shown in FIG. 9, the axis 80 intersects the central longitudinal axis 86 of the viewing channel at the bottom of the channel. The central axis 86 of the viewing channel changes in accordance with the amount of separation between the jaws 20 which is a factor of the degree of pivoting of the movable jaw 20 about the pins 22 and the setting of the fixed jaw element 16 relative to the supporting base 14. Since the axis 86 shifts front to back, depending on the front to back dimension of the viewing channel, the open end 60 of the guide tube 52 is positioned so that the axis 80 of the fiber-optic light beam intersects the axis 86 of the viewing channel at the base of the channel for an average setting of the fixed blade 18 and an average opening angle of the movable blade 20. For other settings, the point of intersection between the axes 80 and 86 will be either above or below the bottom opening of the channel 21. However, regardless of the particular setting of the speculum elements, the light beam axis 80 will always extend through the bottom opening of the channel 21. The lateral position of the axis 86 does not change so that the orientation between the axis 80 of the light beam and the axis 86 of the viewing channel will remain as shown in FIG. 8. The ideal angle between the axis 80 and the axis 86 in the lateral plane as shown in FIG. 8, is between 4° and 6°, depending on the size of the particular speculum being utilized. Since the central axis 80 of the light beam extends down the middle of the viewing channel 21, the areas below the viewing channel and in the immediate vicinity of the channel receive maximum lighting for examination. The use of fiber-optics concentrates the light only in the area to be examined and therefore does not hinder the physician's ability to examine or cause discomfort to the patient. The use of fiber-optics also enables an intense light beam to be used which would not be possible with conventional illumination means such as a flashlight or incandescent lamp. The fiber-optic source 78 is indicated at a remote location from the examination area. The standard commercial fiber-optic light sources are capable of generating a light beam with extremely high intensity. The heat which is normally associated with the creation of high intensity light remains at the light source so that only the visible portion of the electro-magnetic radiation (light) which is generated by the light source 78 is transmitted through the fiber-optic tube 76 and emerges from the open end 60 as the light beam 84. The absence of heat at the examination site avoids a possible source of discomfort to the physician and patient. The use of fiber-optics also enables the examination to take place in an environment in which the presence of electrical equipment could be a hazard, for example, if oxygen is used during the examination. The light source 78 can be located in a location which is sufficiently remote from the examination area so that it does not represent a safety hazard.

The illumination means 50 is applied to the supporting base 14 of the speculum by loosening the nut 42 so that the leg 64 can be inserted between the first upper surface 44 and the nut 42, so that the screw 38 extends into the slot 68. The free end of the leg 64 has a curved lip 67 which has the same radius as the curved surface 49 so that when the nut 42 is tightened, the lip 67 aligns itself with the surface 49 and automatically positions the leg 66 against the outer surface 46 of the side wall 17. When the illumination means 50 is thus positioned, the open end 60 of the tube will be automatically positioned relative to the fixed leg 18 as shown in FIGS. 1 and 2 and, even more graphically, in FIGS. 8 and 9.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Vaginal speculum comprising:
 (a) a supporting base,
 (b) A fixed jaw which is mounted on the supporting base and which extends substantially at a right angle to the supporting base,
 (c) a movable jaw which is generally parallel with the fixed jaw and which is pivotally mounted to the supporting base for movement toward and away from the fixed jaw between a closed postion in which the movable jaw is adjacent the fixed jaw to an open position in which the movable jaw is spaced from the fixed jaw to define an elongated viewing channel between said jaws,
 (d) means for moving the movable jaw away from the fixed jaw to said open position and to maintain the movable jaw in said open postion,
 (e) an elongated fiber-optic guide tube, one end of which is adapted to be connected to a fiber-optic light source, the opposite end of said guide tube having an opening for projecting a beam of light which emanates from said light source and which is transmitted through said guide tube, and
 (f) means for mounting guide tube on said base so that the central axis of said beam of light is within said viewing channel, wherein said guide tube is mounted so that said opposite end is located at the end of said viewing channel which is adjacent said supporting base, and adjacent one lateral side of said viewing channel, said opposite end being adjacent said fixed jaw and bent toward the center of said viewing channel, so that the central axis of said beam of light is substantially in the center of said view channel, wherein said base has a first surface which includes a pair of side edges and a second surface which extends at an angle from one side edge of said first surface, and wherein said mounting means comprises an L-shaped bracket which is fixed to said guide tube, said bracket having a first leg which is adapted to lie against said first surface and a second leg which is adapted to lie against said second surface, said first surface being a determinant of the position of the opposite end of the guide tube relative to said one end of the viewing channel and said second surface being a determinant of the position of the opposite end of the guide tube relative to the central axis of the viewing channel, and (g) means for releasably fastening said bracket to the base.

2. Vaginal speculum as recited in claim 1, wherein said fixed jaw is adjustably mounted on said base for movement toward and away from said movable jaw and said fastening means is effective to clamp said fixed jaw to said base.

3. Vaginal speculum as recited in claim 1, wherein said base has a third surface which extends from the opposite side edge of said first surface at an angle to said first surface and said first leg has a lip which extends at an angle from the free end of said first leg for engaging said opposite side edge.

4. Vaginal speculum as recited in claim 3, wherein said opposite side edge is curved and said lip is curved, said lip and said opposite edge having substantially the same degree of curvature.

5. Fiber-optic light attachment for a vaginal speculum having a supporting base which has first and second surfaces which extend at an angle to each other, a fixed jaw element which is mounted on the supporting base and which has an elongated fixed jaw which extends substantially at a right angle to the supporting base, a fastening element for clamping the fixed jaw to said base, a movable jaw element which is pivotally attached to said base and which has a movable elongated jaw extending generally parallel to the fixed jaw for movement toward and away from said fixed jaw, said fixed jaw element being mounted on said base for movement toward and away from said movable jaw, said fixed and movable jaws defining therebetween an elongated viewing channel having a central longitudinal axis, said fiber-optic light attachment comprising:

(a) an elongated fiber-optic guide tube one end of which is adapted to be connected to a fiber-optic light source and the opposite end of which has an opening for projecting a beam of light, said tube having an intermediate portion which extends along an axis, said opposite end being bent relative to the axis of said straight section, so that the central projecting axis of said beam of light is at an angle to the axis of said straight section, and (b) a mounting bracket fastened to the said supporting base and fixed to the straight section of said tube, said mounting bracket having a first leg which is adapted to lie against said first surface and a second leg which is adapted to lie against said second surface, said first and second legs extending laterally of the axis of said tube and being effective to position the guide tube so that said opposite end of the tube is adjacent the fixed jaw and to one lateral side of the viewing channel, the bend at said opposite end relative to said first and second legs being such that the projecting axis of said light beam extends along said guide channel and intersects the central longitudinal axis of said guide channel.

6. Fiber-optic light attachment for a vaginal speculum having a supporting base which has a first surface and a second surface which extends at an angle from one side edge of said first surface, a fixed jaw element which is slidably mounted on the supporting base and which has an elongated fixed jaw which extends substantially at a right angle to the supporting base, a fastening element which includes a screw for clamping the fixed jaw to said base, a movable jaw element which is pivotally attached to said base and which has a movable elongated jaw which is generally parallel with the fixed jaw for movement toward and away from said fixed jaw, said fixed jaw element being mounted on said base for movement toward and away from said movable jaw, said fixed and movable jaws defining therebetween an elongated viewing channel having a central longitudinal axis, said fiber-optic light attachment comprising:

(a) an elongated fiber-optic guide tube one end of which is adapted to be connected to a fiber-optic light source and the opposite end of which has an opening for projecting a beam of light, said tube having an intermediate portion which extends along an axis, said opposite end being bent relative to the axis of said straight section so that the central projecting axis of said beam of light is at an angle to the axis of said straight section, (b) a mounting bracket which is fixed to the straight section of said tube, said mounting bracket having a first leg which is adapted to lie against said first surface and a second leg which is adapted to lie against said second surface, said first and second legs extending laterally of the axis of said tube and being effective to position the guide tube so that said opposite end of the tube is adjacent the fixed jaw and to one lateral side of the viewing channel, the bend at said opposite end, relative to said first and second legs, being such that the projecting axis of said light beam extends along said guide channel and intersects the central longitudinal axis of said guide channel, and (c) means for fastening said mounting bracket to said supporting base.

7. Fiber-optic light attachment as recited in claim 6, wherein said first surface is substantially flat and is located in a plane which is at a right angle to the central longitudinal axis of said viewing channel and said second surface is substantially flat and is parallel with the central longitudinal axis of said viewing channel and at a right angle to said first surface, said first and second legs being substantially flat and said first leg being at a right angle to said second leg, said opposite end of the guide tube being bent relative to the plane of said second leg and relative to the plane of said first leg.

8. Fiber-optic light attachment as recited in claim 6, wherein the projecting axis of said beam of light extends on an angle of between 4° and 7° relative to the central axis of the viewing channel.

9. Fiber-optic light attachment as recited in claim 6, wherein the means for fastening said mounting bracket to said supporting base comprises an opening in said first leg for receiving the screw of said fastening element and enabling said mounting bracket to be clamped between said fixed jaw element and said base.

10. Fiber-optic light attachment as recited in claim 9, wherein said base has a third surface which extends at an angle from the opposite side edge of said first surface and said first leg has a lip which extends at an angle from the free end of said first leg for engaging said third surface.

11. Fiber-optic light attachment as recited in claim 10, wherein said base has a curved corner between said first and third surfaces and said lip having a curvature which is substantially equal to the curvature of said corner for automatically positioning said bracket on said base in a precise lateral orientation.

* * * * *